United States Patent [19]

Ackermann et al.

[11] 4,378,372
[45] Mar. 29, 1983

[54] CYCLOPROPANECARBOXYLIC ACID ESTERS AND USE THEREOF IN PEST CONTROL

[75] Inventors: Peter Ackermann, Reinach; Laurenz Gsell, Basel; Rudolf Wehrli, Rheinfelden, all of Switzerland

[73] Assignee: Ciba-Geigy Corporation, Ardsley, N.Y.

[21] Appl. No.: 350,451

[22] Filed: Feb. 19, 1982

[30] Foreign Application Priority Data

Feb. 26, 1981 [CH] Switzerland ............... 1298/81
Oct. 13, 1981 [CH] Switzerland ............... 6540/81

[51] Int. Cl.³ .............. A01N 53/00; C07C 69/743; C07C 121/75
[52] U.S. Cl. .............. 424/304; 260/465 D; 424/305; 560/124
[58] Field of Search .......... 260/465 D; 560/124; 424/304, 305

[56] References Cited

U.S. PATENT DOCUMENTS 4,024,163 5/1977 Elliott et al. .............. 260/347.4

Primary Examiner—Dolph H. Torrence
Attorney, Agent, or Firm—Frederick H. Rabin

[57] ABSTRACT

The invention relates to cyclopropanecarboxylic acid esters of the formula

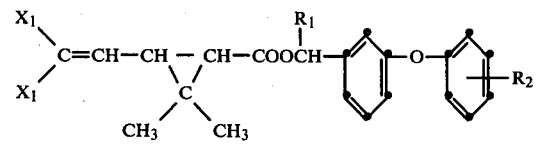

wherein $X_1$ is methyl or halogen, $R_1$ is hydrogen, cyano, $-CSNH_2$, allenyl, $C_2-C_3$alkenyl or $C_2-C_3$alkynyl, and $R_2$ is unsubstituted or substituted alkenyl or alkynyl.

A process for obtaining these compounds and their use in pest control are also disclosed.

10 Claims, No Drawings

CYCLOPROPANECARBOXYLIC ACID ESTERS AND USE THEREOF IN PEST CONTROL

The present invention relates to cyclopropanecarboxylic acid esters of the formula

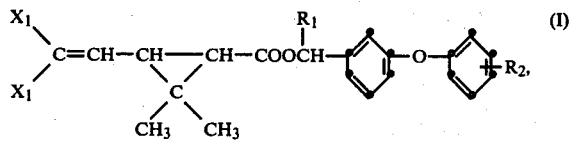

wherein $X_1$ is methyl or halogen, $R_1$ is hydrogen, cyano, —CSNH$_2$, allenyl, C$_2$-C$_3$alkenyl or C$_2$-C$_3$alkynyl, and $R_2$ is unsubstituted or substituted alkenyl or alkynyl, to the production thereof and to the use thereof in pest control.

Halogen in the definition of $X_1$ is fluorine, chlorine or bromine.

The alkenyl or alkynyl groups suitable for $R_1$ and $R_2$ can be straight chain or branched. The alkenyl and alkynyl groups $R_2$ contain in the chain preferably 2 to 6, most preferably 2 to 3, carbon atoms.

Examples of preferred substituents carried by groups $R_2$ are: cyano, bromine, iodine, hydroxyl, C$_1$-C$_6$ alkyl, C$_1$-C$_6$hydroxyalkyl or C$_1$-C$_6$haloalkyl, dimethylamino or phenyl. Particularly preferred alkenyl or alkynyl groups $R_2$ are: vinyl, 1-propenyl, ethynyl, iodoethynyl or 1-propynyl. Preferred compounds of formula I are those wherein $X_1$ is fluorine, chlorine or bromine, $R_1$ is hydrogen or cyano and $R_2$ is vinyl, 1-propenyl, ethynyl, iodoethynyl or 1-propynyl.

Particularly preferred compounds of formula I are those wherein $X_1$ is fluorine, chlorine or bromine, $R_1$ is hydrogen or cyano and $R_2$ is p-vinyl, p-1-propenyl, p-ethynyl, p-iodoethynyl or p-1-propynyl.

The compounds of formula I are obtained by methods which are known per se, e.g. as follows:

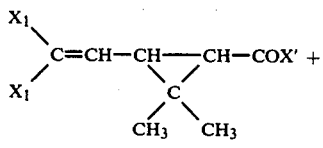

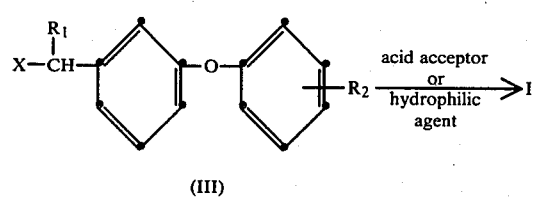

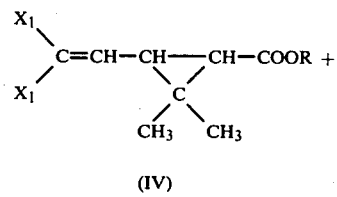

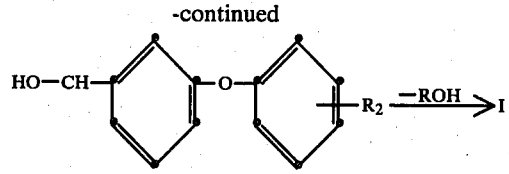

In formulae II to V above, $X_1$, $R_1$ and $R_2$ are as defined for formula I. In formulae II and III each of the symbols X and X' is a hydroxyl group and the other is a halogen atom, preferably a chlorine or bromine atom, and R in formula IV is C$_1$-C$_4$alkyl, preferably methyl or ethyl.

Suitable acid acceptors for process 1 are in particular tertiary amines, such as trialkylamines and pyridine, and also hydroxides, oxides, carbonates and bicarbonates of alkali metals and alkaline earth metals, and in addition alkali metal alcoholates, for example potassium tert-butylate and sodium methylate. As hydrophilic agent for process 1 it is possible to use e.g. dicyclohexylcarbodiimide. Processes 1 and 2 are carried out at a reaction temperature between −10° and 120° C., usually between 20° and 80° C., under normal or elevated pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxamides; aliphatic, aromatic and halogenated hydrocarbons, especially benzene, toluene, xylene, chloroform and chlorobenzene; nitriles such as acetonitrile; dimethyl sulfoxide; and ketones such as acetone and methyl ethyl ketone.

The starting materials of the formulae II to V are known and can be obtained by methods analogous to known ones.

The compounds of the formula I are obtained in the form of a mixture of different optically active isomers if inhomogeneous optically active starting materials are used in the reaction. The different mixtures of isomers can be separated into the individual isomers by known methods. A compound of the formula I will be understood to comprise both the individual isomers and the mixtures thereof.

The compounds of the formula I are suitable for controlling a variety of pests of animals and plants. In particular, the compounds of the formula I are suitable for controlling insects e.g. of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and mites and ticks of the order Acarina.

In particular, the compounds of the formula I are suitable for controlling plant-destructive insects, especially plant-destructive feeding insects, in ornamentals and crops of useful plants, especially in cotton (e.g. *Spodoptera littoralis* and *Heliothis virescens*), vegetables (e.g. *Leptinotarsa decemlineata* and *Myzus persicae*), rice (*Chilo suppressalis* and *Laodelphax striatellus*) and in fruit (e.g. *Laspeyresia pomonella* and Adoxophyes).

The compounds of the formula I are also very effective against flies, for example *Musca domestica* and mosquito larvae.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

Compounds of the formula I are also combined with particular advantage with substances which exert a synergistic or potentiating effect on pyrethroids. Examples of such compounds include: piperonyl butoxide, propynyl ethers, propynyl oximes, propynyl carbamates and propynyl phosphates, 2-(3,4-methylenedioxyphenoxy)-3,6,9-trioxaundecane (Sexamex or Sesoxane), S,S,S-tributylphosphorotrithioate, 1,2-methylenedioxy-4-(2-(octylsulfinyl)-propyl)benzene.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. Just as with the nature of the compositions, the methods of application, such as spraying atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the active ingredient of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives of alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, NJ, 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

FORMULATION EXAMPLES

Formulation Examples for Liquid Active Ingredients of the Formula I (throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 70% | 25% | 20% |

Emulsions of any required concentration can be produced from such concentrates by dilution with water

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160-190°) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for Solid Active Ingredients of the Formula I (throughout, percentages are by weight)

| (5) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (6) Emulsifiable concentrate | |
|---|---|
| active ingredient | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (7) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (8) Extruder granulate | |
|---|---|
| active ingredient | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| (9) Coated granulate | |
|---|---|
| active ingredient | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (10) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

EXAMPLE 1

Preparation of
1-[3'-(p-ethynylphenoxy)benzyl]-2,2-dimethyl-3-(2',2'-dichlorovinyl)cyclopropanecarboxylate 1.26 ml of pyridine and then a solution of 2.7 g of the compound of the formula

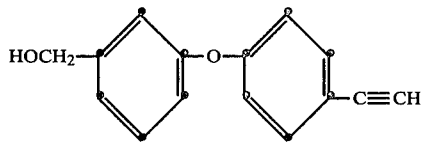

in 20 ml of toluene are added dropwise in succession, at 0° C., to a solution of 2.74 g of the compound of the formula

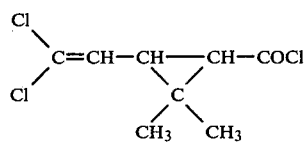

in 20 ml of toluene. The reaction mixture is stirred for 12 hours at 20° C. and then poured into 2 N hydrochloric acid and extracted once with each of 10% potassium carbonate, saturated sodium bicarbonate and saturated sodium chloride solution. The organic phase is dried over magnesium sulfate, filtered and concentrated. The crude product is chromatographed on silica gel with toluene as eluant, to give the compound of the formula

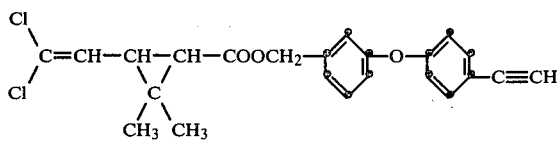

with a refractive index of $n_D^{20°} = 1.5841$.

The following compounds are prepared in analogous manner:

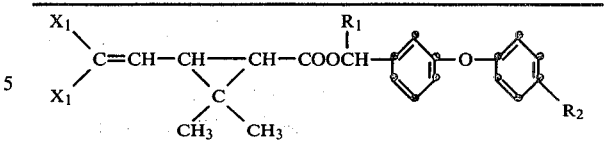

| $X_1$ | $R_1$ | $R_2$ | Physical data |
|---|---|---|---|
| Cl | CN | —C≡CH | $n_D^{20°} = 1.5809$ |
| Cl | CN | —C≡C—CH$_3$ | $n_D^{30°} = 1.5770$ |
| Br | CN | —C≡CH | $n_D^{30°} = 1.5916$ |
| Br | CN | —C≡C—CH$_3$ | $n_D^{20°} = 1.5969$ |
| F | CN | —C≡CH | $n_D^{25°} = 1.5530$ |
| F | CN | —C≡C—CH$_3$ | $n_D^{30°} = 1.5525$ |
| Cl | CN | —CH=CH$_2$ | $n_D^{25°} = 1.5741$ |
| Cl | CN | —C≡Cl | $n_D^{30°} = 1.600$ |
| Cl | H | —CH=CH—CH$_3$ | $n_D^{20°} = 1.5790$ |
| CH$_3$ | CN | —C≡CH | $n_D^{30°} = 1.5613$ |
| Cl | CN | —CH=CH—CH$_3$ | $n_D^{20°} = 1.5762$ |
| Cl | —C≡CH | —C≡C—CH$_3$ | $n_D^{30°} = 1.5819$ |
| Cl | —CH=C=CH$_2$ | —C≡C—CH$_3$ | $n_D^{30°} = 1.5899$ |
| Cl | H | —CH=CH$_2$ | $n_D^{30°} = 1.5781$ |
| Cl | CN | —C≡C—CH$_2$—N(CH$_3$)$_2$ | $n_D^{30°} = 1.5668$ |
| Cl | CN | —C≡C—CH$_2$—N(CH$_3$)$_2$ | $n_D^{30°} = 1.5679$ |

EXAMPLE 2

Insecticidal stomach poison action against *Laspeyresia pomonella*

10 diet cubes are sprayed with a test solution containing 10, 50, 100, 200 or 400 ppm of the compound to be tested. After the spay coating has dried, each cube is populated with 2 larvae of the species *Laspeyresia pomonella* (L$_1$ stage). A mortality count is made 48 hours later. The test is carried out at 24° C. and 60% relative humidity.

The compounds obtained in the preparatory Example act against larvae of *Laspeyresia pomonella* as shown in the following Table.

BIOLOGICAL TEST RESULTS

Test results based on the preceding Example are reported in the table, using the following rating to indicate the percentage kill of the pests:

A: 70–100% kill at a concentration of 10 ppm
B: 70–100% kill at a concentration of 50 ppm
C: 70–100% kill at a concentration of 100 ppm
D: 70–100% kill at a concentration of 200 ppm
E: 70–100% kill at a concentration of 400 ppm.

Compounds

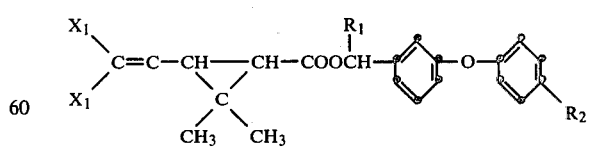

| $X_1$ | $R_1$ | $R_2$ | Action against *Laspeyresia pomonella* L$_1$-larvae |
|---|---|---|---|
| Cl | H | —C≡CH | A |
| Cl | CN | —C≡CH | A |
| Cl | CN | —C≡C—CH$_3$ | A |

-continued

A: 70–100% kill at a concentration of 10 ppm
B: 70–100% kill at a concentration of 50 ppm
C: 70–100% kill at a concentration of 100 ppm
D: 70–100% kill at a concentration of 200 ppm
E: 70–100% kill at a concentration of 400 ppm.

Compounds

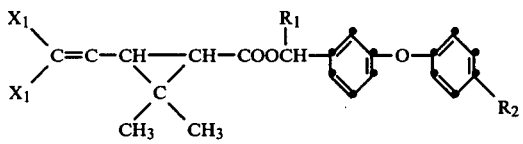

| $X_1$ | $R_1$ | $R_2$ | Action against *Laspeyresia pomonella* $L_1$-larvae |
|---|---|---|---|
| Br | CN | $-C\equiv CH$ | A |
| Br | CN | $-C\equiv C-CH_3$ | A |
| F | CN | $-C\equiv CH$ | A |
| F | CN | $-C\equiv C-CH_3$ | A |
| Cl | CN | $-CH=CH_2$ | B |
| Cl | CN | $-C\equiv CI$ | A |
| Cl | H | $-CH=CH-CH_3$ | A |
| $CH_3$ | CN | $-C\equiv CH$ | A |
| Cl | CN | $-CH=CH-CH_3$ | A |
| Cl | $-C\equiv CH$ | $-C\equiv C-CH_3$ | E |
| Cl | $-CH=C=CH_2$ | $-C\equiv C-CH_3$ | E |

What is claimed is:

1. A cyclopropanecarboxylic acid ester of the formula

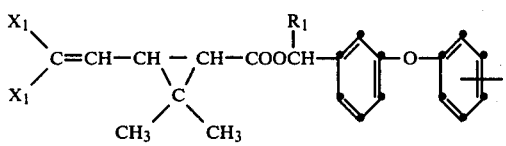

wherein $X_1$ is methyl or halogen, $R_1$ is hydrogen, cyano, $-CSNH_2$, allenyl, $C_2-C_3$alkenyl or $C_2-C_3$alkynyl, and $R_2$ is unsubstituted or substituted alkenyl or alkynyl.

2. A compound according to claim 1, wherein $X_1$ is fluorine, chlorine or bromine, $R_1$ is hydrogen or cyano and $R_2$ is vinyl, 1-propenyl, ethynyl, iodoethynyl or 1-propynyl.

3. A compound according to claim 2, wherein $X_1$ is fluorine, chlorine or bromine, $R_1$ is hydrogen or cyano and $R_2$ is p-vinyl, p-1-propenyl, p-ethynyl, p-iodoethynyl or p-1-propynyl.

4. The compound according to claim 3 of the formula

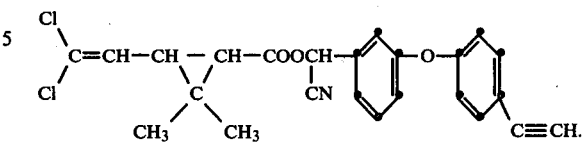

5. The compound according to claim 3 of the formula

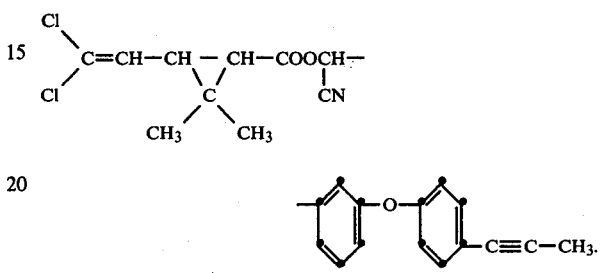

6. The compound according to claim 3 of the formula

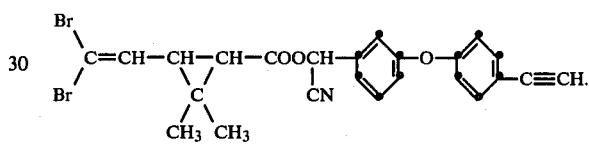

7. The compound according to claim 3 of the formula

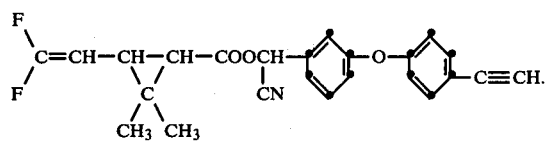

8. The compound according to claim 3 of the formula

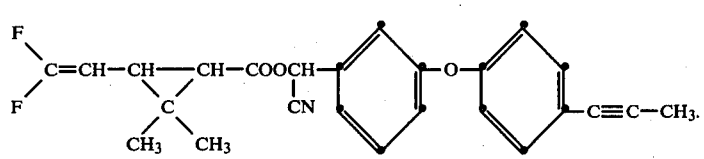

9. A pesticidal composition which contains, as active component, a compound according to claim 1.

10. A method of controlling pests of animals and plants, which comprises applying thereto a pesticidally effective amount of a compound according to claim 1.

* * * * *